(12) United States Patent
Piantoni et al.

(10) Patent No.: US 12,365,147 B2
(45) Date of Patent: Jul. 22, 2025

(54) ULTRASONIC WELDING SYSTEM

(71) Applicant: GDM S.p.A, Bologna (IT)

(72) Inventors: Matteo Piantoni, Albino (IT); Alessandro Zavalloni, Sesto ed Uniti (IT)

(73) Assignee: GDM S.P.A., Bologna (IT)

(*) Notice: Subject to any disclaimer, the term of this patent is extended or adjusted under 35 U.S.C. 154(b) by 139 days.

(21) Appl. No.: 18/485,476

(22) Filed: Oct. 12, 2023

(65) Prior Publication Data
US 2024/0123693 A1    Apr. 18, 2024

(30) Foreign Application Priority Data

Oct. 18, 2022  (IT) .................. 102022000021480

(51) Int. Cl.
*B29C 65/08* (2006.01)
*B29C 65/00* (2006.01)

(52) U.S. Cl.
CPC .......... *B29C 66/9511* (2013.01); *B29C 65/08* (2013.01)

(58) Field of Classification Search
CPC ... B29C 65/08; B29C 65/087; B29C 65/7885; B29C 66/9511; B29C 66/9513; B29C 66/9674
USPC .......................................................... 156/64
See application file for complete search history.

(56) References Cited

U.S. PATENT DOCUMENTS

| 7,383,865 B2 * | 6/2008 | Umebayashi ..... B29C 66/92613 |
| | | 156/580.2 |
| 9,943,447 B2 * | 4/2018 | Fujita ................ B29C 66/83511 |

FOREIGN PATENT DOCUMENTS

WO    2020/165749 A1    8/2020

OTHER PUBLICATIONS

Italian Search Report from related IT Application No. 202200021480, dated May 3, 2023, 8 pages.

* cited by examiner

*Primary Examiner* — James D Sells
(74) *Attorney, Agent, or Firm* — Dilworth IP, LLC (57) ABSTRACT

An ultrasonic welding system and method for making welds on a strip made of polymeric material. The system includes a supporting structure, N welding equipment mounted thereon, and a processor. Each N welding equipment includes a pair of welding heads made of a sonotrode, including a sonotrode welding surface, and an anvil, including an anvil welding surface. One of the two welding heads is movable with respect to the other between a non-operating position and a welding position. A control member is operatively associated with the sonotrode and configured to vibrate the sonotrode at a nominal ultrasonic vibration frequency and to detect a current value of the vibration frequency. A vibration sensor is mounted on the movable welding head. The processor monitors the alignment condition between the sonotrode welding surface and the anvil welding surface by cooperating with the control member and with the vibration sensor.

13 Claims, 3 Drawing Sheets

ULTRASONIC WELDING SYSTEM

FIELD OF THE INVENTION

The invention concerns an ultrasonic welding system, a production line for articles comprising such a welding system and a welding method.

BACKGROUND OF THE INVENTION

In particular, the invention relates to an ultrasonic welding system for making welds on a strip made of polymeric material during the advancement thereof.

For example, the system of the present invention can be used to weld a continuous strip in a transverse direction, with respect to a direction in which the strip is advanced, according to a certain welding pitch.

Such a system can be used, for example, to make welds in a production line for absorbent hygiene articles, or nappies, in particular to make the welding of sidebands of pull-up nappies.

According to further examples, the system of the present invention can be used to weld a continuous strip for making food and confectionery articles, such as chocolates or sweets; bottles and cartons of beverages; pouches containing solid, liquid or semi-solid foodstuffs; articles from the tobacco industry; articles from the cosmetics industry; articles from the pharmaceutical industry; articles from the personal & home care industry.

For example, the system of the present invention can be used to make welds in flowpack-type product packaging machines.

These flowpack type machines are configured to fold a continuous packaging film in tubular form surrounding a sequence of products to be packaged. In these packaging machines, the packaging film is closed in tubular form around the products to be packaged by joining, usually overlapping, the longitudinal edges of the film and welding them together. On the tubular packaging film thus formed, a plurality of transverse welds are made between one product and the next in such a way as to separate each product (or group of products) from the others. Transverse cuts are made at the transverse welds to obtain individual product packages.

WO 2020/165749 describes a rotary device for welding absorbent articles comprising a member rotating about its own axis of rotation, one or more supporting elements of a continuous strip of absorbent articles, supported by the rotating member, and a plurality of welding units of the continuous strip supported by the rotating member. Each welding unit is configured to switch between non-operating and operating positions. Each welding unit comprises a respective welding terminal and a respective contrast element, which is movable relative to the welding terminal. Each welding unit comprises respective first movement means configured to control a relative rotation of the contrast member with respect to the welding terminal from an initial position, at which the contrast member is angularly distanced from the welding terminal, to an end position, at which the surface of the welding terminal and the surface of the contrast member are parallel and aligned along the same alignment axis.

The Applicant has noted that in order to ensure a uniform weld of good quality, it is important that in the operating position, where the welding surfaces of two welding heads contact a strip interposed between them in order to weld, these weld surfaces are in an alignment condition where they are parallel to each other and aligned along the same alignment axis, which is orthogonal to them. However, there are situations in which incorrect settings or wear problems of certain components of the welding device can cause misalignments with respect to the alignment condition. These misalignments can lead to defective (e.g. uneven) welds, which are qualitatively unacceptable.

The Applicant therefore perceived the need to provide an improved welding system, particularly in terms of reliability, precision and quality.

SUMMARY OF THE INVENTION

From a number of experiments and studies carried out on an ultrasonic welding device with welding equipment each comprising two welding heads made from a sonotrode and an anvil, one of which is movable with respect to the other, the Applicant surprisingly found that situations of misalignment between the two welding surfaces of the two welding heads generate a variation of mechanical vibration of the movable welding head during its movement from a non-operating position (in which the two welding heads are spaced apart from each other) to a welding position (in which the two welding heads are in contact with each other and engage the continuous strip to be welded). The Applicant also found that misalignment situations generate a variation in the welding frequency of the sonotrode compared to a nominal value for which the device is set.

The Applicant has therefore found that the above-mentioned need can be met by an ultrasonic welding system in which any misalignment between two welding surfaces of two welding heads of a welding equipment is detected by monitoring the mechanical vibrations of the movable welding head during its movement from a non-operating position to a welding position and/or by monitoring the welding frequency of the sonotrode in the welding position.

The present invention therefore relates, in a first aspect thereof, to an ultrasonic welding system.

Preferably, the welding system is adapted to perform a weld on a strip made of polymeric material.

Preferably, the welding system comprises a supporting structure.

Preferably, the welding system comprises N welding equipment mounted on said supporting structure, with integer N at least equal to 1.

Preferably, the welding system comprises a processor.

Preferably, the N welding equipment each comprise a pair of welding heads made of a sonotrode, comprising a sonotrode welding surface, and an anvil, comprising an anvil welding surface.

Preferably, in each of the N welding equipment, one movable welding head between the two welding heads of each pair of welding heads is movable with respect to the other welding head of the pair between a non-operating position and a welding position, and vice versa.

Preferably, in the non-operating position, the sonotrode welding surface and the anvil welding surface are spaced apart.

Preferably, in the welding position, the sonotrode welding surface and the anvil welding surface are in contact with each other, to engage the strip, and in an alignment condition.

Preferably, each of the N welding equipment comprises a control member operatively associated with the respective sonotrode, said control member being configured to vibrate the sonotrode at a nominal ultrasonic vibration frequency and to detect a current value of the vibration frequency of the sonotrode.

Preferably, the processor is configured to monitor, for each pair of welding heads, the alignment condition between the sonotrode welding surface and the anvil welding surface.

Preferably, the processor is operatively connected to the control member of each of the N welding equipment and is configured to determine, for each pair of welding heads, the presence of a misalignment with respect to the alignment condition if, while the movable welding head is staying in the welding position, the current value of the vibration frequency of the sonotrode detected by the control member is outside a respective acceptable range with respect to the nominal ultrasonic vibration.

Alternatively or additionally, each of the N welding equipment comprises a vibration sensor which is mounted on the movable welding head of the respective pair of welding heads and is operatively connected to the processor, the processor being configured to determine the presence of a misalignment with respect to the alignment condition if vibrations detected by the vibration sensor during the movement of the movable welding head between the non-operating position and the welding position have values outside a respective acceptable range.

The present invention relates, in a second aspect thereof, to a production line for articles made of polymeric material.

Preferably, the line comprises an ultrasonic welding system according to the first aspect of the invention.

Preferably, the line comprises a feeding system to feed the strip made of polymeric material to said welding system.

Preferably, the line includes at least one cutting device upstream and/or downstream of the welding system.

The present invention relates, in a further aspect thereof, to an ultrasonic welding method for making welds on a strip made of polymeric material.

Preferably, a pair of welding heads are provided, made of a sonotrode, comprising a sonotrode welding surface, and an anvil, comprising an anvil welding surface.

Preferably, it is provided to feed said strip between the sonotrode and anvil welding surfaces.

Preferably, it is provided to move one movable welding head of the pair of welding heads with respect to the other welding head of the pair of welding heads between a non-operating position and a welding position, and vice versa.

Preferably, in the non-operating position, the sonotrode welding surface and the anvil welding surface are spaced apart.

Preferably, in the welding position, the sonotrode welding surface and the anvil welding surface are in contact with each other, to engage the strip and in an alignment condition.

Preferably, when the movable welding head is in the welding position, it is provided to vibrate the sonotrode at a nominal ultrasonic vibration frequency.

Preferably, it is provided to check the alignment condition between the sonotrode welding surface and the anvil welding surface by at least one of the following steps:
  detecting a current value of the sonotrode ultrasonic vibration frequency when the movable welding head is in the welding position and determining the presence of a misalignment with respect to the alignment condition if the current value of the detected sonotrode vibration frequency is outside a respective acceptable range with respect to the nominal ultrasonic vibration; and
  detecting vibrations of the movable welding head during the movement of the movable welding head between the non-operating position and the welding position and determining the presence of a misalignment with respect to the alignment condition if the vibrations detected have values outside a respective acceptable range.

The present invention advantageously enables the detection of any misalignment between two welding surfaces of two welding heads of an ultrasonic welding system by monitoring the mechanical vibrations of the movable welding head during its movement from a non-operating position to a welding position and/or by monitoring the welding frequency of the sonotrode when the movable welding head is in the welding position.

In view of the fact that the mechanical vibrations of the moving welding head can be monitored with a vibration sensor, such as an accelerometer, which is readily available on the market at low cost, and that the welding frequency of the sonotrode can be monitored by taking advantage of the sonotrode control unit, which is already typically present in an ultrasonic welding device in any case, to adjust the vibration of the sonotrode to a nominal ultrasonic vibration frequency, the invention advantageously allows for the detection of misalignments in a simple and cost-effective manner.

The Applicant further notes that the invention advantageously allows for real-time information on any misalignments that could generate welding defects so that the presence of a misalignment and possible defective welds can be promptly reported and/or immediate action can be taken on the welding system in order to remedy the detected misalignment and to stop the production of defective welds.

In addition, the Applicant notes that welding defects—not being visible—are not directly detectable using machine vision techniques (i.e. image processing techniques). These defects, in order to be detected, would require advanced and costly inspection devices or checks carried out in the laboratory, outside the production line, which are typically performed on sample products to test the strength of a weld by mechanically measuring, by means of conventional tensile tests, the maximum tensile force the weld is able to withstand until failure.

Compared to such solutions, the invention advantageously enables the on-line and automated detection of non-visible welding defects without requiring the use of advanced and expensive inspection devices and without having to mechanically and manually intervene on the articles by means of conventional tensile tests on sample products.

Overall, this achieves the above objectives of improving an ultrasonic welding system, particularly in terms of reliability, precision and quality.

"Strip" is used to indicate either a raw material, in the form of a single continuous or discrete strip-like element, for the formation of an article in production, or a semi-finished strip-like article at any stage of the relevant production process within a production line. The article may be an absorbent hygiene article, a container or wrapper for food products, an article from the tobacco industry, the cosmetics industry or the pharmaceutical industry, and may comprise one or more strip-like elements made of polymeric material.

The term "substantially flat" referring to a welding surface is used to indicate either a perfectly flat surface, or a generally flat surface that has at least one step/level-difference to compensate for any differences in material thicknesses in the area to be welded, or a surface defined by several flat surfaces separated from each other that can fit independently of each other to compensate for any differences in material thicknesses of the strip to be welded.

"Polymeric material" refers to a material made of natural or synthetic polymer.

The terms "radial" and "radially" are used to indicate references/measurements/sizes arranged/measured or extending in a direction that intersects the axis of rotation of a rotating structure of the welding system and is contained in a plane perpendicular to that axis of rotation.

The present invention may have, in the aspects discussed above, at least one of the preferred features described below. These characteristics may therefore be present individually or in combination with each other, unless expressly stated otherwise.

The polymeric material may be a natural polymeric material, such as cotton, cellulose and derivatives, or a synthetic polymeric material such as, for example, polyolefins (e.g., polyethylene and polypropylene), polyesters (e.g., polyethylene terephthalate and polylactic acid), polyamides, acrylics, polyethers and copolymers of two or more of the materials cited as examples.

Preferably, the movable welding head of each pair of welding heads is the anvil. In an alternative embodiment, the movable welding head of each pair of welding heads is the sonotrode.

In a preferred embodiment, the vibration sensor is an accelerometer.

Preferably, the sonotrode welding surface and the anvil welding surface are substantially flat.

An alignment condition is defined as a condition in which the sonotrode and anvil welding surfaces are parallel to each other and/or are aligned with respect to the same alignment axis orthogonal to them. Misalignment occurs when the sonotrode welding surface and the anvil welding surface are not parallel to each other and/or are not aligned with respect to the same alignment axis orthogonal to them.

In one embodiment, the supporting structure is rotating about its own axis of rotation. Preferably, N welding equipment are mounted on said rotating supporting structure so that they are transported in rotation by said supporting structure.

In one embodiment, the processor is configured to determine the presence of said misalignment in the event that the vibrations detected by the vibration sensor have values outside the respective acceptable range during a final step of movement of the movable welding head between the non-operating position and the welding position.

Preferably, in this final step the welding surface of the movable welding head comes into contact with the welding surface of the other welding head of the pair of welding heads (and with the strip interposed between the two surfaces).

Preferably, said final step is performed by means of a translation movement.

Preferably, the N welding equipment each include a mechanism for moving the respective movable welding head between the non-operating and the welding position.

In an embodiment, in each of the N welding equipment, the movement mechanism is configured to move the respective welding head according to a first rotation movement and according to a second translation movement. The first movement is preferably adapted to perform a first movement step of the movable welding head between the non-operating position and the welding position. The second movement is preferably adapted to perform a final movement step of the movable welding head between the non-operating position and the welding position.

In an embodiment, the movement mechanism comprises a gripper mechanism that is movable between an open configuration, corresponding to the non-operating position, and a closed configuration, corresponding to the welding position.

In an embodiment, the N welding equipment protrude radially from the supporting structure.

When $N>1$, the N welding equipment are preferably angularly spaced around the axis of rotation; preferably they are equally spaced from each other.

Preferably, the N welding equipment cyclically follow a closed loop trajectory during the rotation of said supporting structure about said axis of rotation.

Preferably, said closed trajectory defines at least in part a strip's advancement trajectory.

The N welding equipment can be radially movable with respect to the axis of rotation, towards the axis of rotation and away from it, e.g. to vary the extension of the closed trajectory.

In an embodiment, when $N>1$, the device comprises a plurality of supporting elements of the continuous strip interposed between the N welding equipment.

In a preferred embodiment, in each pair of welding heads, the sonotrode is in a radially internal position with respect to the anvil.

In a preferred embodiment, in each pair of welding heads, the sonotrode faces radially inwards with respect to the supporting structure and the anvil faces radially outwards with respect to the supporting structure.

The production line preferably comprises production devices configured to perform respective production operations on the articles being processed along the production line.

Preferably, the production line comprises transport members adapted to support and move the articles being processed along the production line.

Preferably, the transport members are associated with retention devices configured to hold the articles being processed in position on a supporting surface of the transport members.

Preferably, an alarm signal will be generated when a misalignment is determined.

Preferably, when the presence of a misalignment is determined, a corrective action to be taken to remedy the misalignment is defined.

BRIEF DESCRIPTION OF THE FIGURES

Further characteristics and advantages of the present description will become clearer from the following detailed description of the preferred embodiments thereof, with reference to the appended drawings and provided by way of indicative and non-limiting example, in which.

DETAILED DESCRIPTION OF THE INVENTION

Figure 1:
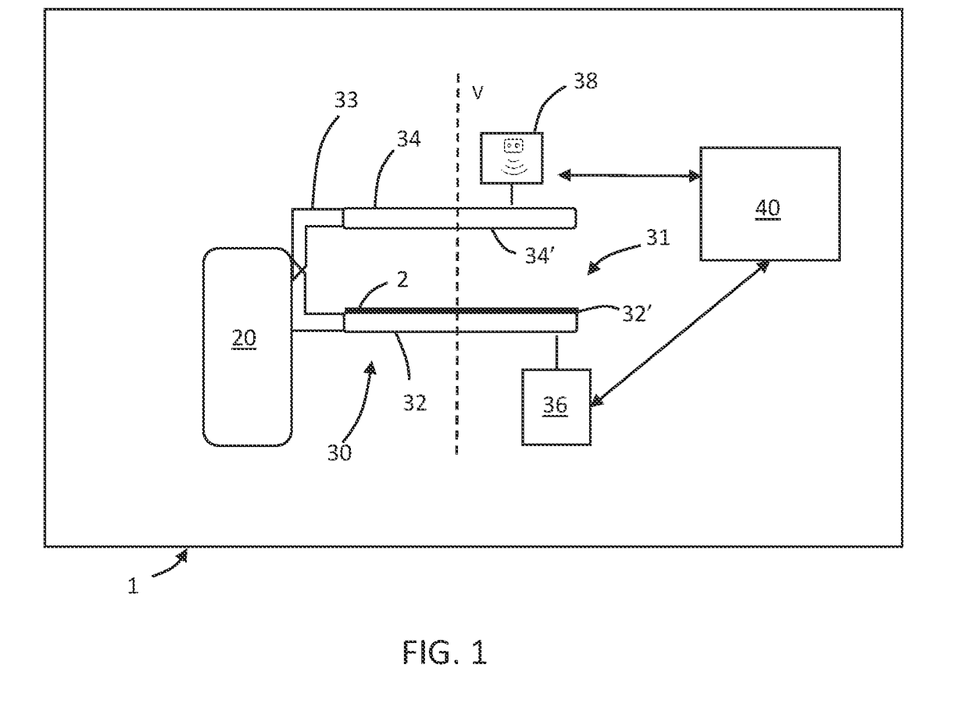
FIG. 1 schematically shows an ultrasonic welding system according to an embodiment of the present invention.

FIG. 1 schematically shows an ultrasonic welding system 1 according to an embodiment of the present invention, adapted to perform welds on a strip 2 made of polymeric material.

The system 1 comprises a supporting structure 20, a processor 40 and N welding equipment 30 mounted on said supporting structure 20, where N is an integer at least equal to 1. For simplicity of illustration, the situation of N=1 is shown in FIG. 1.

The N welding equipment 30 each comprise a pair of welding heads 31 made of a sonotrode 32, comprising a sonotrode welding surface 32', and an anvil 34, comprising an anvil welding surface 34'.

In the embodiment illustrated, the sonotrode 32 has a flat sonotrode welding surface 32' and the anvil 34 has a flat anvil welding surface 34', both of which engage the strip 2 to be welded.

The sonotrode welding surface 32' preferably has a specific welding pattern to be imprinted onto the strip 2 in the areas to be welded.

In the illustrated embodiment, the anvil 34 defines a movable welding head that is movable relative to the sonotrode 32 between a non-operating and a welding position, and vice versa.

Figure 2:
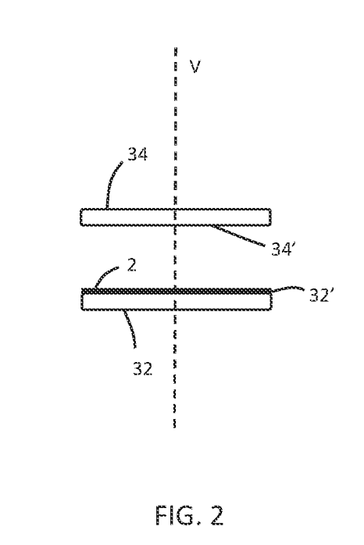
FIGS. 2 and 3 schematically show a sonotrode welding surface and an anvil welding surface of a pair of welding heads of the welding system of FIG. 1 in two situations where the respective movable welding head is in a non-operating and a welding position, respectively.

As schematically illustrated in FIG. 2, in the non-operating position, the flat sonotrode welding surface 32' and the flat anvil welding surface 34' are arranged opposite to each other on opposite sides of the strip 2 to be welded.

Figure 3:
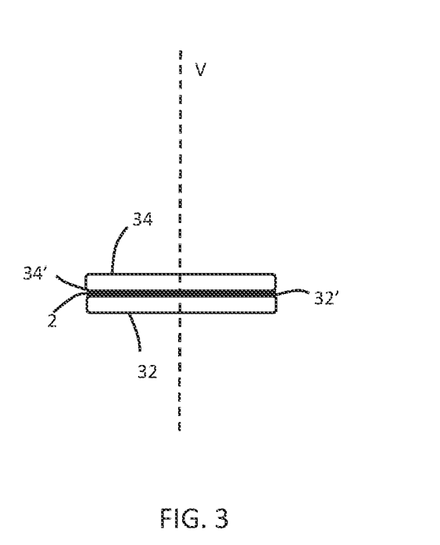

As schematically illustrated in FIG. 3, in the welding position, the flat sonotrode welding surface 32' and the flat anvil welding surface 34' are in contact with each other to engage the strip 2 and in an alignment condition.

In the alignment condition, the flat sonotrode welding surface 32' and the flat anvil welding surface 34' are parallel to each other and aligned with respect to a common alignment axis V, orthogonal to them. In particular, in the embodiment illustrated, the alignment axis V coincides with a centreline of the two surfaces 32', 34'.

Each of the N welding equipment 30 comprises a movement mechanism 33 (shown only schematically in FIG. 1) of the anvil 34 between the non-operating position and the welding position and vice versa.

For example, the movement mechanism 33 may be configured to move the anvil 34 according to a translational movement along a direction parallel to the alignment axis V, or according to a first rotational movement and according to a second translational movement, or according to a rotational movement by means of a gripper mechanism.

In the presence of a rotary movement, at the non-operating position, the flat sonotrode welding surface of 32' and the flat anvil welding surface 34', in addition to being spaced apart, may be incident (situation not illustrated).

In the presence of a translation movement, at the non-operating position, the flat sonotrode welding surface 32' and the flat anvil welding surface 34' are not only spaced apart, but also parallel to each other (situation illustrated in FIGS. 2-3).

Each of the N welding equipment 30 comprises a control member 36 operatively associated with the respective sonotrode 32.

The control member 36 is configured to make the sonotrode 32 vibrate at a nominal ultrasonic vibration frequency when the anvil 34 is in the welding position to make welds on the strip 2 pressed between the anvil 34 and the sonotrode 32.

The nominal ultrasonic vibration frequency may be comprised between 10 and 50 kHz, preferably between 25 and 35 KHz.

The control member 36 also monitors the current value of the vibration frequency of sonotrode 32 so as to detect any deviations from the nominal ultrasonic vibration frequency.

The control member 36 is of the type conventionally used in ultrasonic welding devices comprising a sonotrode and an anvil.

According to the invention, each of the N welding equipment also comprises a vibration sensor 38 which is mounted on the anvil 34.

The vibration sensor 38 is, for example, an accelerometer. The accelerometer can be uniaxial, bi-axial or triaxial.

For example, the vibration sensor 38 is a low-impedance accelerometer of the type known in the art.

The processor 40 is operatively connected to the vibration sensor 38 and the control member 36 to monitor, for each pair of welding heads 31, the alignment condition between the sonotrode welding surface 32' and the anvil welding surface 34'.

In particular, the processor 40 is configured to detect, for each pair of welding heads 31, the presence of a misalignment, with respect to the alignment condition, in the event that:

while the anvil 34 is in the welding position, the current value of the vibration frequency of the sonotrode 32 detected by the control member 36 is outside a respective acceptable range with respect to the nominal ultrasonic vibration frequency; and/or the vibrations detected by the vibration sensor 38 during the movement of the anvil 34 between the non-operating position and the welding position have values outside a respective acceptable range.

Experiments and studies carried out by the Applicant have shown that the presence of a misalignment (i.e., a non-parallelism between the sonotrode welding surface 32' and the anvil welding surface 34' and/or a non-alignment with respect to the alignment axis V) generates a variation of the order of a few tenths of the nominal ultrasonic vibration frequency of the sonotrode 32. The vibration frequency variation is at least two-tenths of the nominal vibration frequency.

Furthermore, the presence of such a misalignment causes, during the movement of the anvil 34 from the non-operating position to the welding position, a variation in vibration of the anvil 34 of the order of a few tenths with respect to a predetermined reference value. The vibration frequency variation is at least two-tenths of the predetermined reference value. This reference value represents a nominal vibration value of the anvil 34 (or of the movable head in general) in an alignment condition.

In particular, it was found that in the case of misalignment, an abnormal vibration (with respect to the nominal vibration value) of the anvil 34 can be detected in a final part of its movement from the non-operating position to the welding position, where the anvil welding surface 34' comes into contact with the sonotrode welding surface 32'.

Once the presence of a misalignment is detected, the processor 40 is configured to perform at least one of the following actions: generate an alarm signal; generate a warning signal that potentially defective welds are being made; automatically stop the welding system 1; define, by means of appropriate algorithms, a corrective action to be taken to remedy the misalignment; signal the corrective action to be taken; indicate (e.g. by means of a display, not illustrated) a sequence of step-by-step instructions to guide an operator in implementing the corrective action.

Within an article production line, the processor 40 can also generate a warning signal about the need to discard articles currently in production and/or automatically stop the production line 1.

The strip 2 may be a continuous or discrete strip-like element. Furthermore, the strip 2 may be a single starting element (a raw material) for the formation of a polymeric material article or a semi-finished polymeric material article at any stage of the relevant production process within a production line. The articles could be absorbent hygiene articles or other types of articles made of polymeric material such as containers or wrappers for food products.

For example, in flowpack-type wrapping machines, the strip 2 could comprise a tubular wrapping film surrounding a sequence of products to be packaged on which a plurality of transverse welds are made between one product and the next in order to separate each product (or group of products) from the others.

Figure 5:
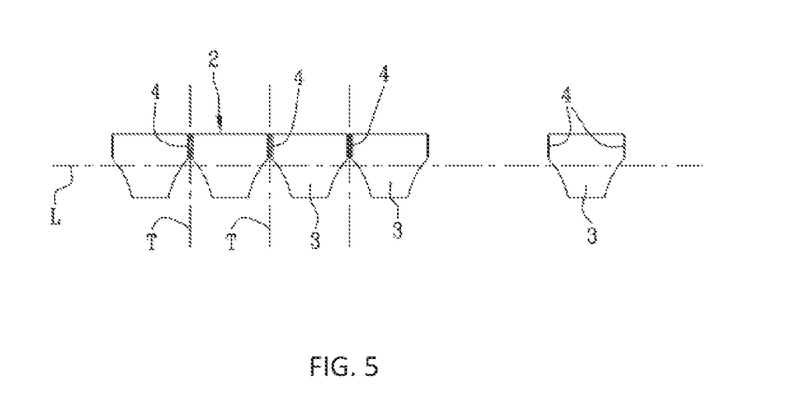
FIG. 5 shows in a schematic plan view a continuous strip 2 of absorbent hygiene articles that can be welded by the welding system of FIG. 4.

In the example illustrated in FIG. 5, the strip 2 to be welded is a continuous strip of absorbent sanitary articles, in particular a continuous strip 2 of pull-up nappies, so-called "training pants".

The continuous strip 2 is presented as a succession of absorbent articles 3 folded at the centreline of an absorbent pad.

The continuous strip 2 has a prevailing longitudinal L-shaped extension.

In this case, the welding system 1 is configured to weld the continuous strip 2 of absorbent sanitary articles in a transverse direction "T" with respect to the longitudinal extension direction "L".

In particular, with reference to FIG. 5, the welding system 1 can be used to make a plurality of welds in the transverse direction "T" of the continuous strip 2 in respective welded zones 4, each of which is intended to define the transverse weld of overlapping elastic bands of respective absorbent articles 3.

These welded zones 4 are required to seal the elastic bands of the absorbent article 3 at the hips of the end-user.

In other embodiments not illustrated, the strip 2 may consist of basic elements of an absorbent hygiene article that must be welded together. Such basic elements may comprise a first sheet of permeable material, a second sheet of impermeable material, intended to define, respectively, the inner and outer faces of the absorbent hygiene article, and a third element consisting of an absorbent padding interposed between the first and second sheets. Alternatively or additionally, the strip 2 may comprise additional elements for the formation of an absorbent hygiene article, which may vary in number and form, and preferably comprise front and/or rear flaps, acquisition and distribution layers or reinforcement layers or other discrete elements typically provided in absorbent hygiene articles between the first sheet and the second sheet.

Figure 4:
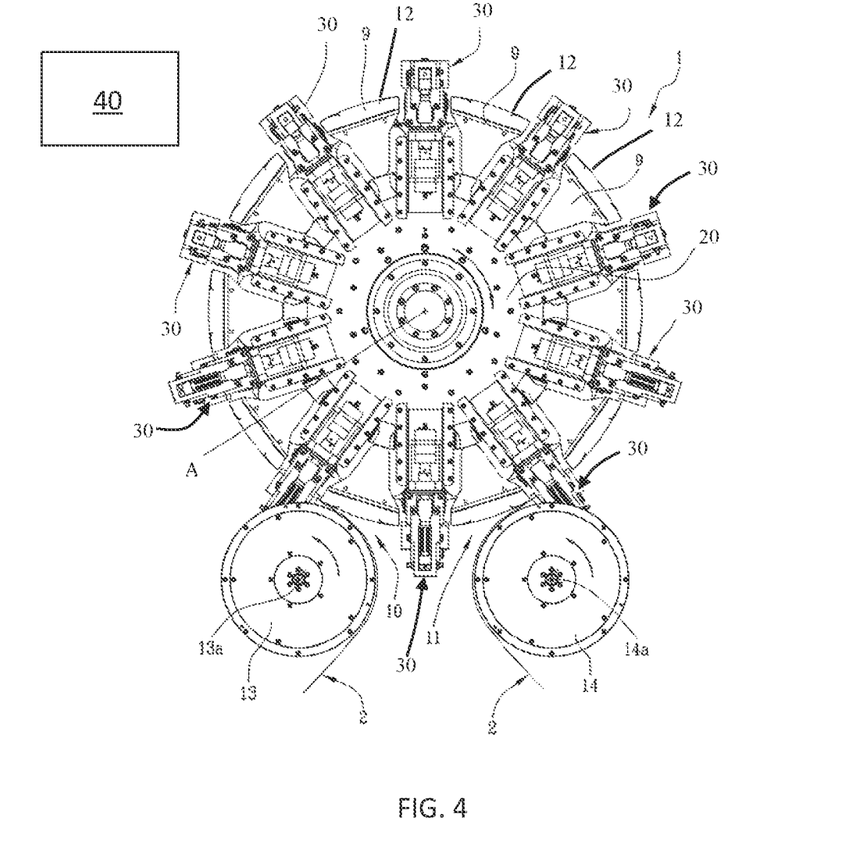
FIG. 4 shows schematically in a front schematic view an example of an embodiment of the ultrasonic welding system of FIG. 1.

FIG. 4 describes by way of example a welding system 1 for a continuous strip 2 wherein the supporting structure 20 is rotating about its own axis of rotation A and the N welding equipment 30 (with N=10) are mounted on said supporting structure 20 so as to be rotatably transported by it.

For simplicity of illustration, the presence of the processor 40 is illustrated schematically.

The N welding equipment 30 are angularly equally spaced from each other with respect to the axis of rotation A of the supporting structure 20.

The circumferential arrangement pitch of the N welding equipment 30 around the rotation axis A corresponds to the pitch of the welds to be made on the strip 2. For example, in the example of FIG. 5, the circumferential arrangement pitch of the N welding equipment 30 around the axis of rotation A corresponds to the pitch of the welded zones 4 of the continuous strip of absorbent articles 3.

In each of the N welding equipment 30, the sonotrode welding surface 32' defines a contact and supporting surface for a respective portion of the continuous strip 2.

In each of the N welding equipment 30, the sonotrode 32 is arranged radially inward relative to the supporting structure 20 while the anvil 34 is arranged radially outward relative to the supporting structure 20.

In each of the N welding equipment 30, at the non-operating position of the respective anvil 34, the anvil welding surface 34' is arranged relatively far apart from the sonotrode welding surface 32' while the latter contacts a relative portion of the continuous strip 2 by pulling it into rotation.

In each of the N welding equipment 30, at the welding position of the respective anvil 34, the anvil welding surface 34' and the sonotrode welding surface 32' contact a respective portion of continuous strip 2 interposed between them to make the welds.

In the embodiment of FIG. 4, the welding system 1 also comprises a plurality of elements 9 supporting the continuous strip 2.

The elements 9 supporting the continuous strip 2 are supported by the supporting structure 20 and consequently rotate about the axis of rotation A.

The N welding equipment 30 and the supporting elements 9 are arranged angularly spaced from each other.

In other words, each welding equipment 30 is interposed between a respective pair of support elements 9.

Each support element 9 has a retaining surface 12 of the continuous strip 2.

The retaining surface 12 of each support element 9 is preferably a curved surface.

Alternatively, the retaining surface 12 of each support element 9 may be a flat surface.

Preferably, the support elements 9 are configured to hold the continuous strip 2 by suction. As such, the retaining surface 12 may have a pattern of holes (not illustrated) for suction.

The welding system 1 comprises a feeding station 10 of the continuous strip 2 to be welded and an outlet station 11 of the welded continuous strip 2.

The continuous strip 2 is fed through the feeding station 10 by means of a roller 13, preferably of the suction type, rotating about its own axis 13a, so that the continuous strip 2 to be welded is wrapped, without slipping, around the retaining surface 12 of the support elements 9.

The welded continuous strip 2 is fed through the outlet station 11 by a roller 14, preferably of the suction type, rotating about its own axis 14a.

The axis of rotation 13a of the roller 13 and the axis of rotation 14a of the roller 14 are parallel. The axis of rotation A of supporting structure 20 is parallel to the axes of rotation 13a, 14a.

Figure 6:
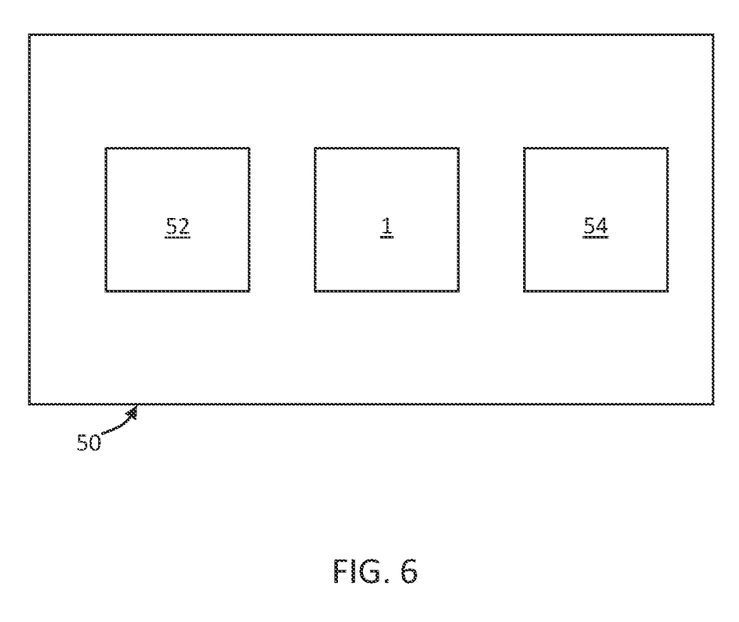
FIG. 6 schematically illustrates a line for producing articles according to an embodiment of the invention.

As schematically illustrated in FIG. 6, the welding system 1 may be used within a production line 50 of articles made of polymeric material to perform welds on a continuous strip 2 made of polymeric material.

In addition to the ultrasonic welding system 1, the production line 50 may comprise a feeding system 52 for supplying the continuous strip 2 to the welding system 1 and at least one cutting device 54 downstream of the welding system 1.

By way of example, FIG. 6 shows a single cutting device 54 downstream of the welding system 1, configured to cut the continuous strip 2 after welding, e.g. to make cuts or weakening lines on the continuous strip 2, so that joined articles being processed, resulting from the production process, can subsequently be separated or made easily separable into individual articles.

For example, in the case of the continuous strip 2 of FIG. 5, the cutting device 54 is adapted to separate each absorbent item 3 from the other by acting at each welded area 4 of the continuous strip 2, in particular at the centreline of each.

Upstream of the welding system 1, the production line 50 may also include feeding devices (not shown) adapted to feed starting materials or individual strip-like elements to production devices (not shown) adapted to form the strip 2.

Alternatively or additionally, the production line 50 may comprise at least one cutting device (not shown) upstream of the welding system 1 configured to cut said starting materials for the production of individual elements or for shaping individual elements.

The following describes how the welding system 1 makes welds on the strip 2 at one of the N welding equipment 30.

Initially, the anvil 34 (in the illustrated embodiment representing the movable welding head) is placed in the non-operating position, i.e. away from the sonotrode 32.

The strip 2 is placed above the sonotrode welding surface 32'.

The anvil 34 is then moved to the welding position, where the anvil welding surface 34' presses the strip 2 to be welded against the sonotrode welding surface 32'.

During the movement of the anvil 34 between the non-operating position and the welding position, vibrations of the anvil 34 are detected.

When the anvil 34 is in the welding position, the sonotrode 32 is vibrated at a nominal ultrasonic vibration frequency and the current value of the sonotrode's ultrasonic vibration frequency is monitored.

The alignment condition between the sonotrode welding surface 32' and the anvil welding surface 34' is monitored and a misalignment is detected if—as explained in detail above—at least one of the two conditions occurs:
- the current value of the vibration frequency of the sonotrode 32 is outside a respective acceptable range with respect to the nominal ultrasonic vibration; and
- the measured vibrations of the anvil 34', during its movement between the non-operating and the welding position, have values outside a respective acceptable range.

The invention claimed is:

1. An ultrasonic welding system for making welds on a strip made of polymeric material, the welding system comprising a supporting structure, N welding equipment mounted on said supporting structure, with integer N at least equal to 1, and a processor, wherein:
   the N welding equipment each comprise a pair of welding heads made of a sonotrode, comprising a sonotrode welding surface, and an anvil, comprising an anvil welding surface;
   in each of the N welding equipment, one movable welding head between the two welding heads of each pair of welding heads is movable with respect to the other welding head of the pair between a non-operating position and a welding position, and vice versa, wherein:
      in the non-operating position, the sonotrode welding surface and the anvil welding surface are spaced apart; and
      in the welding position, the sonotrode welding surface and the anvil welding surface are in contact with each other, to engage the strip, and in an alignment condition;
   each of the N welding equipment comprises a control member operatively associated with the respective sonotrode, said control member being configured to vibrate the sonotrode at a nominal ultrasonic vibration frequency and to detect a current value of the vibration frequency of the sonotrode;
   the processor is configured to monitor, for each pair of welding heads, the alignment condition between the sonotrode welding surface and the anvil welding surface;
and wherein the welding system comprises at least one of the following features:
   the processor is operatively connected to the control member of each of the N welding equipment and is configured to determine, for each pair of welding heads, a presence of a misalignment with respect to the alignment condition if, while the movable welding head is staying in the welding position, the current value of the vibration frequency of the sonotrode detected by the control member is outside a respective acceptable range with respect to the nominal ultrasonic vibration; and
   each of the N welding equipment comprises a vibration sensor which is mounted on the movable welding head of the respective pair of welding heads and is operatively connected to the processor, the processor being configured to determine the presence of a misalignment with respect to the alignment condition if vibrations detected by the vibration sensor during a movement of the movable welding head between the non-operating position and the welding position have values outside a respective acceptable range.

2. The welding system according to claim 1, wherein the movable welding head of each pair of welding heads is the anvil.

3. The welding system according to claim 1, wherein the vibration sensor is an accelerometer.

4. The welding system according to claim 1, wherein in the alignment condition the sonotrode welding surface and the anvil welding surface are parallel to each other and/or are aligned with respect to a same alignment axis orthogonal thereto.

5. The welding system according to claim 1, wherein the sonotrode welding surface and the anvil welding surface are substantially planar.

6. The welding system according to claim 1, wherein the supporting structure is rotatable about a rotation axis thereof and the N welding equipment is mounted on said supporting structure so as to be rotatably transported by said supporting structure.

7. The welding system according to claim 1, wherein the processor is configured to determine the presence of said misalignment if the vibrations detected by the vibration sensor have values outside the respective acceptable range during a final movement step of the movable welding head between the non-operating position and the welding position, said final step being performed by means of a translation movement.

8. The welding system according to claim 1, wherein the N welding equipment each comprises a movement mechanism of the respective movable welding head between the non-operating position and the welding position.

9. The welding system according to claim 8, wherein in each of the N welding equipment, the movement mechanism is configured to move the respective welding head according to a first rotation movement and according to a second translation movement.

10. A production line of articles made of polymeric material comprising:
    the ultrasonic welding system according to claim 1;
    a feeding system adapted to feed the strip made of polymeric material to said welding system;
    at least one cutting device upstream and/or downstream of the welding system.

11. An ultrasonic welding method for making welds on a strip made of polymeric material, comprising:
    providing a pair of welding heads made of a sonotrode, comprising a sonotrode welding surface, and an anvil, comprising an anvil welding surface;
    feeding said strip between the sonotrode welding surface and the anvil welding surface;
    moving one movable welding head of the pair of welding heads with respect to the other welding head of the pair of welding heads between a non-operating position and a welding position, and vice versa, wherein:
        in the non-operating position, the sonotrode welding surface and the anvil welding surface are spaced apart; and
        in the welding position, the sonotrode welding surface and the anvil welding surface are in contact with each other, to engage the strip, and in an alignment condition;
    when the movable welding head is in the welding position, vibrating the sonotrode at a nominal ultrasonic vibration frequency;
    checking the alignment condition between the sonotrode welding surface and the anvil welding surface (34') by at least one of the following steps:
        detecting a current value of the sonotrode ultrasonic vibration frequency when the movable welding head is in the welding position and determining a presence of a misalignment with respect to the alignment condition if the current value of the detected sonotrode vibration frequency is outside a respective acceptable range with respect to the nominal ultrasonic vibration; and
        detecting vibrations of the movable welding head during the movement of the movable welding head between the non-operating position and the welding position and determining the presence of a misalignment with respect to the alignment condition if the vibrations detected have values outside a respective acceptable range.

12. The welding method according to claim 11, comprising a generation of an alarm signal when the presence of a misalignment is determined.

13. The welding method according to claim 11, comprising, when a misalignment is determined, a definition of a corrective action to be adopted to remedy the misalignment.

* * * * *